United States Patent [19]

Klus et al.

[11] 4,416,148
[45] Nov. 22, 1983

[54] SURFACE TENSIOMETER

[75] Inventors: John P. Klus, Madison; Everett E. Gibbons, Monona; Eric L. Brodsky, Madison; Victor P. Janule, Sun Prairie, all of Wis.

[73] Assignee: Madison-Kipp Corporation, Madison, Wis.

[21] Appl. No.: 232,091

[22] Filed: Feb. 6, 1981

[51] Int. Cl.³ .......................................... G01N 13/02
[52] U.S. Cl. .................................................. 73/64.4
[58] Field of Search ........................................ 73/64.4

[56] References Cited

U.S. PATENT DOCUMENTS

| 3,276,844 | 10/1966 | Davison et al. ............. | 73/64.4 X |
| 3,380,463 | 4/1968 | Trethewey . | |
| 3,426,584 | 2/1969 | Smith ........................... | 73/64.4 |
| 3,765,227 | 10/1973 | Campbell et al. ............. | 73/64.4 |
| 3,881,344 | 5/1975 | Jobe ............................. | 73/64.4 |

FOREIGN PATENT DOCUMENTS

| 462115 | 9/1975 | U.S.S.R. ........................ | 73/64.4 |
| 603879 | 4/1978 | U.S.S.R. ........................ | 73/64.4 |
| 661302 | 5/1979 | U.S.S.R. ........................ | 73/64.4 |

OTHER PUBLICATIONS

Padday, J. F., *Surface Tension (Parts I & II)* in Surface and Colloid Science, vol. 1, pp. 39-149, 1969.
Sudgen, S., *Determ. of Surface Tension from Max. Press. in Bubbles* in J. Chem. Soc., vol. 121, pp. 859-867, 1922 and vol. 123, pp. 27-31, 1923.
Cuny et al., *Bubble-Pressure Method of Surface Tension*, NASA TT S-13, 937, pp. 1-28, 1956.
Schork et al., *Monit. Emul. Polym. Reactor Dyn.*, Presented at Meeting of Amer. Chem. Soc., 1980.
Schwaneke et al., *Improv. Max.-Bubble-Press. for Surface Tension*, Bureau of Mines Report No. RI-7340, pp. 1-9, 1980.
Razouk, R., *App. for Determ. Surface Tension*, NASA Tech Briefs, pp. 508-509, 1977.

Primary Examiner—Anthony V. Ciarlante
Assistant Examiner—Joseph W. Roskos
Attorney, Agent, or Firm—Biebel, French & Nauman

[57] ABSTRACT

Apparatus for measuring the surface tension of a liquid contained in a flow-through pressure vessel (60) includes a pair of tubes (50,51) having small and large orifices positioned below the surface of the liquid. A source (10) provides gas through a pressure regulator (15) and a flow regulator (30) to the tubes. The bubble rate from the orifices is controlled by needle valves (40,41) and is made independent of the pressure in the vessel by the flow regulator (30). Differential pressure transducer (70) measures the pressure in the tubes as an indication of surface tension. Check valves (72,73) protect the transducer, and a thermometer (65) measures liquid temperature.

5 Claims, 10 Drawing Figures

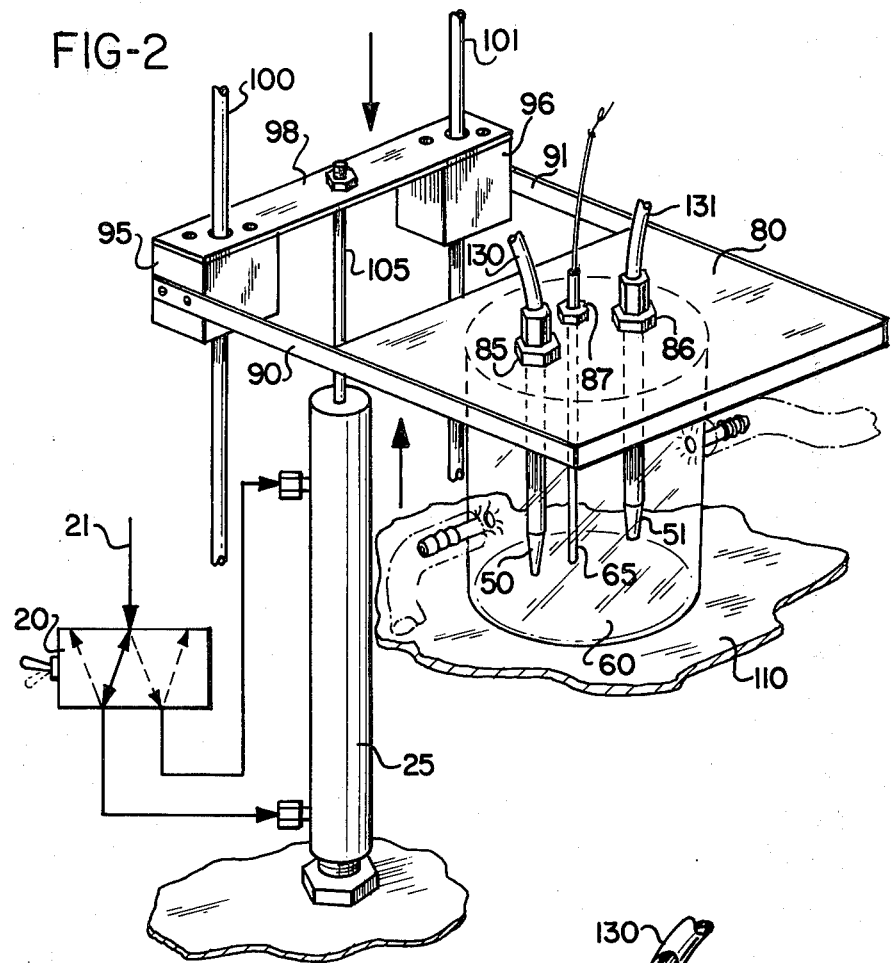
FIG-2
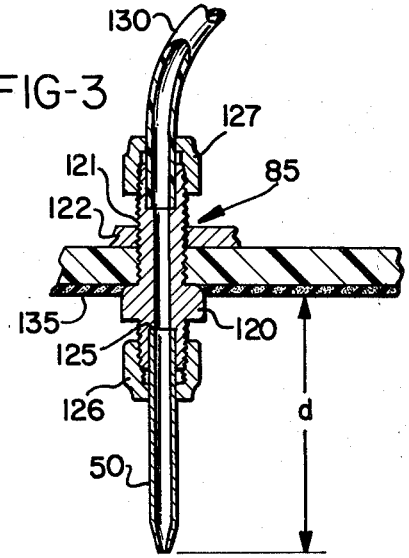
FIG-3
FIG-4

SURFACE TENSIOMETER

BACKGROUND OF THE INVENTION

Surface tension effects were recognized centuries ago and recorded by Leonardo da Vinci (1452–1519) who observed the rise of a fluid in a small tube, which was subsequently termed "capillarity." The forces of adhesion and cohesion in fluids were later recognized by Sir Isaac Newton (1642–1727). The maximum bubble pressure method of measuring surface tension was first suggested by Simon in 1851 and later developed by Jaeger in 1917. The theory had earlier been developed by Cantor in 1892. Sugden, in 1921, developed apparatus that utilized the technique to measure surface tension in fluids in a laboratory setting.

Present laboratory methods for making intermittent (single fluid sample) surface tension measurements include the Wilhelmy Plate method, Du Noüy ring, sessile drop, pendant drop, capillary height, drop weight, and maximum bubble pressure.

No continuous process instrument for measuring surface tension is presently being marketed; only laboratory units using techniques mentioned earlier.

U.S. Pat. No. 3,426,584 suggests a double tube bubble pressure method with two orifices submerged into the liquid at the same depth, with accuracies claimed to be "about two percent."

An instrument using two unequal sized orifice tubes immersed in a process fluid at the same horizontal depth through which process gas is bubbled had been suggested for use in a chemical engineering laboratory environment using a flow-through vessel in which a process liquid is introduced in a continuous stream and into which gas bubbles are introduced under the fluid surface using two fixed orifices of different diameters. This arrangement required precise manual valve adjustments to produce bubbling of gas through the orifices and fluid flow through the cell at the desired rate. Accuracy of this device is claimed to be in the 1–2% range.

There is a need for an on-line surface tension measurement device with in-process accuracies of one percent or less with ½ dyne precision—levels never previously achieved by any prior art techniques—but there is not presently available to industry any such a device, for use in an ongoing process environment, especially where the pressure within the vessel holding the liquid or the liquid level may vary while the surface tension measurements are being made.

In order to measure surface tension accurately in an in-process, on-line environment, it is necessary that the method chosen be as immune as possible to external environmental and other potential contaminating effects. For example, there is sufficient grease from one's finger to lower the surface tension of water from 72 dynes/cm to well below 65 dynes/cm after touching a clean water surface when measurements are made using a surface film measurement technique.

The maximum bubble pressure method, or a variation thereof, can avoid such error-causing effects by measuring surface tension within the body of the test fluid if accurate pressure measurements related to surface tension, due to the gas bubble—fluid interface, can be made. No method to date, however, had completely resolved the physical problems associated with blowing a bubble of gas inside a fluid body and measuring the maximum bubble pressure of this bubble with sufficient accuracy so that all of the effects influencing the pressure value, such as liquid density, radius of the bubble tube orifice, gravitational constant and depth of bubble formation are fully and accurately identified, measured, and resolved.

The basic equation describing surface tension can be written as follows, and is a multiple term, non-linear equation, referred to hereafter as the modified Schroedinger equation:

$$\gamma = \frac{P_1 - P_2}{2(1/r_1 - 1/r_2)} - \frac{\rho g(h_1 - h_2)}{2(1/r_1 - 1/r_2)} + \frac{\rho g(r_2 - r_1)}{3(1/r_1 - 1/r_2)} + \frac{\rho^2 g^2(r_2^3 - r_1^3)}{24 \gamma(1/r_1 - 1/r_2)}$$

Where:
$\gamma$ is the surface tension
$\rho$ is the density of the liquid
$P_1$ is the maximum pressure of bubble at small orifice
$P_2$ is the maximum pressure of bubble at large orifice
$r_1$ is the radius of the small orifice
$r_2$ is the radius of the large orifice
$(h_1 - h_2)$ is the difference in depth of the orifices
$g$ is the gravitational constant As can be seen by the above modified Schroedinger equation, an apparatus that measures surface tension directly must resolve the non-linear multiple terms in this equation. If the orifices are at the exact same height, the second term in the above equation is eliminated.

Orifices must be designed in such a manner that the bubbles produced are ones of constant and consistent size. If a fluid has good wetting properties the end of the capillary tube will be wetted so that the radius of the formed bubble will be the internal tube radius of the orifice. As the liquid recedes to the outer edge, with decreased wetting properties, the bubble radius will approach the outside tube radius of the orifice. This effect was recognized in the surface tension measurement apparatus described in U.S. Pat. No. 2,401,053.

Orifices of previously designed apparatus were designed incorporating fixed tube orifice ratios, either as part of the beaker assembly, or as part of the entire apparatus assembly. The Smith U.S. Pat. No. 3,426,584 fixed the ratio and limited the size of the orifices ($r_1 < 0.01$ cm, $r_2 < 0.2$ cm) in an attempt to negate the second and third terms of the equation used in his patent. This does not recognize that ideally the small orifice must be as small as possible because as the bubble gets smaller, it becomes more spherical and the back pressure due to surface tension effects approaches the value $2\gamma/r$, where r is the radius of the orifice.

A single small orifice pressure equation can be written as $P = \rho g h + 2\gamma/r$, and therefore, if the larger of the two orifices can be used to measure the head (h) effect the smaller orifice will approach more accurately the true surface tension value, $2\gamma/r$. The limitation in practice comes about by physical orifice configurations, fluids that may tend to coagulate and plug orifices, and pneumatic control system configurations.

If the ratios of the two orifices are small (as the sizes decrease in difference) the signals generated become closer in magnitude requiring more electronic filtering and more costly and complicated electronics.

Different orifice sizes will result in different magnitudes of error for the constant term (third term) and non-linear term (fourth term) in the surface tension equation. By using very large and very small orifice sizes, the error terms can be reduced substantially. The error, even if reduced, however, must still be considered if accurate surface tension values are desired. Conversely, if one orifice cannot be very large and the other very small because of physical or fluid considerations mentioned earlier, the error term calculation must correct for inaccurate apparatus output values either manually using a correction chart, or electronically.

Fixed orifices that are fixed as part of the fluid containment vessel lack flexibility because cleaning is more difficult when process fluids change, or different intermittent measurements are required.

Pneumatic control of the bubble rate of the process gas is important for accuracy of surface tension readings. As the level of fluid changes (changing head), increased back pressure will slow down or stop the bubble rate. This precludes the use of existing prior art measurement systems under conditions where varying head or varying pressure conditions exist, such as in pressurized in-process or in-reactor applications. Regulating equipment that will regulate pressure accurately can allow higher pressure or higher head conditions but still will not work well under pressure fluctuation systems. Regulators will compensate for incoming process gas fluctuations but not downstream fluctuations at the orifice.

Proximity of the orifices to one another must be considered since some vibration resonance occurs as bubbles break off at the orifice and rise to the fluid surface. This causes acoustic coupling effects that can add error signals at the sensing transducer. Additionally, the orifices cannot be located too close to the side of the fluid containment vessel so as to impede the free forming and free release of the gas bubble. Motion of the fluid, as in a flow-through vessel, must be such that it does not shear the bubbles from the orifice tips as they form and thereby reduce the desired spherical bubble shape.

Bubbles at the orifice must be formed in a controlled manner. When a fluid-gas surface is formed, a finite time is required to establish equilibrium in the surface phase, and during this period the surface tension is time dependent. The bubble frequency must, therefore, be kept low enough to allow discrete independent bubbles to form.

The pressure signals formed at the small and large orifices take the approximate form of saw-tooth waves. While a differential pressure transducer will subtract the output signals, the net result will still be in the form of a saw-tooth output of very low frequency. Attention must, therefore, be given to the response of any filter circuit that is used to time-average the differential output signal. Cutoff frequency must be low enough to filter out transients and harmonics while time delay must compromise between response and stability.

As the surface area of a pure liquid is increased adiabatically and work is performed on the liquid system, the temperature will drop and the surface tension will increase to constrain expansion. This effect explains the relationship between surface tension and temperature and why, therefore, the surface tension of pure liquids will generally increase as the temperature decreases and vice versa. It is, therefore, necessary to recognize and deal with the surface tension-temperature relationship when surface tension measurements are made.

Existing measurement methods, such as the Du Noüy ring, capillary height and others previously mentioned, require a clear surface without surface contaminants in order to obtain accurate surface tension measurements. These methods, therefore, cannot be used in instances where surface foaming occurs or surface debris is present. These methods will measure surface tension at the topmost level of the test vessel fluid and cannot indicate whether the fluid itself is homogeneous or the reading is due only to a thin surface film, which may have different properties than the bulk of the fluid.

SUMMARY OF INVENTION

The surface tensiometer of this invention allows either continuous or intermittent measurement of surface tension of fluids at ambient conditions or at higher or varying pressures and temperatures under laboratory, pilot plant, laboratory-reactor, or production line conditions. This invention allows measurement of the surface tension of liquids even with surface foam and insoluble surface contaminants. The liquid may be contained within either flow-through sensing vessels or in standard laboratory-type containment beakers and vessels. Associated electronic circuitry produces a display of surface tension directly in dynes per centimeter and a simultaneous display of the temperature of the liquid being monitored.

In a preferred embodiment of the invention, a pair of hollow tubes or probes having orifices of different diameters are positioned the same distance below the surface of the liquid. Process gas is supplied to the tubes to cause bubbles to be formed in the liquid, and the differential pressure in the tubes is measured as a function of the surface tension of the liquid. Actually the pressure in the small orifice tube when the bubble breaks away is measured and compared to the pressure at the large orifice as a function of surface tension; and therefore the large orifice tube serves as the means for determining the pressure at the small orifice. Thus, the two tube emodiment is a convenient apparatus for making these measurements.

A pneumatic system provides process gas flow at both orifices in a controlled, constant volume flow. A constant-differential flow controller is used in conjunction with a low-flow micrometering valve to make the gas flow independent of downstream pressure. Therefore, changes in back pressure at the orifices, due to changing pressure conditions or fluid level, will not substantially effect the gas flow rate or the bubble rate. Separate metering valves at each orifice control the bubble time-rate frequency selection and bubble rate ratio of the large to small orifice.

The pneumatic system preferably includes cascaded pressure regulators at the process gas input point to control and regulate the process gas pressure to a fraction of any incoming pressure variation and allow an inexpensive, high degree method of incoming flow regulation. For example, with a 100% incoming pressure variation, the output pressure can be controlled to within ±2.5%.

The pneumatic system further includes a micrometering needle valve in combination with a constant differential flow controller. The valve acts as a finely tunable variable restriction that can be set to produce the desired flow rate since the flow controller will maintain a constant pressure drop across the needle valve. If the pressure drop across the valve is held constant, the flow through the needle valve will be constant, thus allowing a constant volumetric flow to the tensiometer orifices, independent of downstream pressure. Flow rates adjustable in the range of 5 to 30 cubic centimeters per minute can be accurately maintained by this method.

It is therefore an object of this invention to provide an apparatus for determining the surface tension of a liquid comprising a pressure vessel for containing the liquid, a tube having an orifice positioned below the surface of the liquid, means for providing a source of gas under pressure to said tube, means connected between said source of gas and said tube for controlling the bubble rate of the gas to the tube independently of the pressure within said vessel, means for determining the pressure of the liquid at said orifice, and means for measuring the pressure in said tube as compared to the pressure at said orifice as a function of the surface tension of the liquid.

It is a further object of the invention to provide a surface tensiometer of the type described wherein the orifices may or may not be positioned the same distance below the surface of the liquid.

Other objects and advantages of the invention will be apparent from the following description, the accompanying drawings and the appended claims.

BRIEF DESCRIPTION OF THE DRAWINGS

FIG. 2 is a perspective view of a laboratory version of the invention illustrating a lifting device for supporting the surface tension sensing probes and thermometer in a flow-through vessel.

FIG. 3 is a cross-sectional view showing a probe mounted in the lifting mechanism of FIG. 2.

FIG. 4 is a detailed view of the end of one of the probes.

DESCRIPTION OF THE PREFERRED EMBODIMENT

Figure 1:
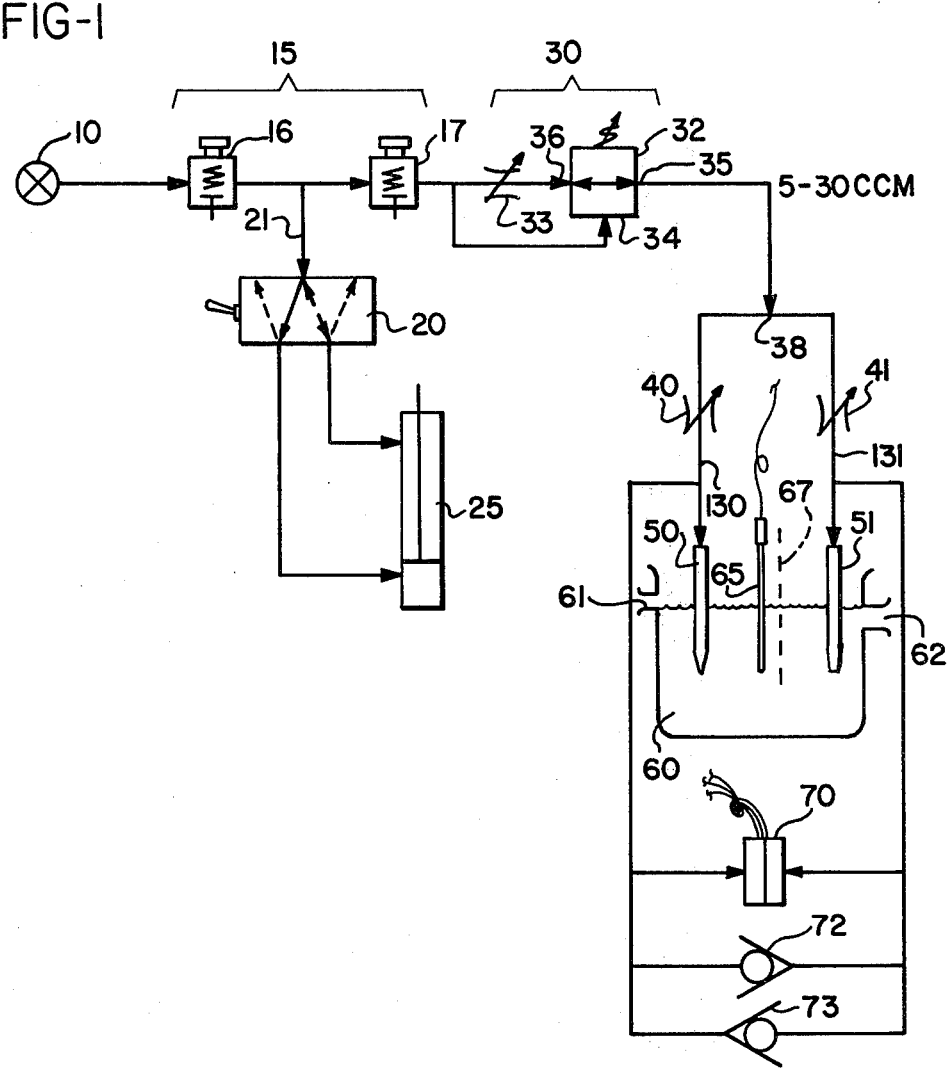
FIG. 1 is a schematic pneumatic diagram illustrating the components comprising a preferred embodiment of the invention.

Referring now to the drawings which illustrate a preferred embodiment of the invention, and particularly to FIG. 1, an apparatus for determining the surface tension of a liquid includes a source of process gas 10 which is connected through appropriate tubing or hoses to pressure regulator means 15 including a pair of cascaded pressure regulators 16 and 17. The gas is typically compressed air from a gas tank or other appropriate source.

The pressure regulators 16 and 17 are cascaded in order to provide a high degree of pressure regulation. For example, with this arrangement, a 100% change in source pressure will not cause more than a 2.5% variation in output pressure. In a preferred embodiment of the invention, type R14 miniature regulators manufactured by Norgren permit an input gas pressure of up to 400 psig to be maintained at a substantially constant predetermined output pressure in the range of from 3 to 95 psig.

A pneumatic switch 20 is connected to the output of pressure regulators 16 by hose 21. The switch controls the position of lifting cylinder 25, the purpose of which will be more fully described later.

The invention also includes means 30 for providing a regulated, constant flow of gas to the remainder of the apparatus. The means 30 includes a flow controller 32 and a micrometering needle valve 33. The flow controller 32 has an input port 34, an output port 35, and a reference port 36. In the preferred embodiment, a Model 63BU flow controller manufactured by Moore Products Co. is used since that device provides a constant gas flow if provided with a constant upstream reference pressure. The reference pressure for this device is provided by the micrometering needle valve 33. Since the flow controller will maintain a constant differential and the pressure across the micrometering needle valve, a high-quality valve, such as a Model MV5 micrometering valve manufactured by Veriflo Corporation, is employed. The gas flow rate is typically set at 5 to 30 cubic centimeters per minute (ccm).

The output of the flow regulator is applied through a T-fitting 38 or other flow dividing means to a pair of fine metering valves 40 and 41. These valves control the gas flow to the orifices at the ends of probes 50 and 51, respectively, and thus provide a variable restriction for controlling the bubble rate at the orifice of each probe. Typically, a bubble rate of approximately one bubble per second is established, and this is done prior to calibration of the instrument.

The liquid under test is contained in a pressure vessel 60 which may be of the flow-through type including an input fitting 61 and an output fitting 62. A flow-through vessel of this type allows dynamic measurement of process fluids, and further allows a "fresh" surface to form at each successive bubble-fluid interface without exposure to or influence by external contaminating conditions.

A temperature probe 65 is provided to sense the temperature of the liquid under test since the surface tension of a liquid is usually temperature dependent. A baffle 67 is preferably placed between the ends of the two probes 50 and 51 to permit the bubbles to be properly formed and to break freely without restriction and without shearing due to the flowing of the liquid through the vessel.

The pressure differential within the probes 50 and 51 is measured by means of a differential pressure transducer 70. Since the differential pressure transducer can measure the differential pressures at relatively high line pressures, but cannot accept high differential pressures which might occur if one of the orifices became plugged by coagulation or impurities in the liquid, a pair of reversed paralleled check valves 72 and 73 are connected across the transducer in order to protect it against over pressure conditions. In the preferred embodiment, these check valves may be set at 0.5 psi.

Referring now to FIG. 2, the probes 50 and 51 and the temperature probe 65 are secured to a support block 80 by means of bulkhead fittings 88, 86 and 87. The support block is connected by means of brackets 90 and 91 to nylon bearing blocks 95 and 96 which in turn are connected together by means of a connecting plate 98. The bearing blocks ride on guide rods 100 and 101. The piston of the double-acting cylinder 25 is connected by shaft 105 to the connecting plate 98, and as the toggle valve 20 is activated, air pressure is directed into the double-acting cylinder to raise or lower the support block 80 and thus the probes 50, 51, and 65 out of or into the liquid contained in the pressure vessel 60.

The flow-through vessel 60 is supported on a horizontal platform 110. It is essential that the orifices at the end of each of the probes 50 and 51 be at the same depth below the surface of the liquid under test in order to eliminate the second term in the modified Schroedinger equation by setting $h_1 = h_2$. This is accomplished in a preferred embodiment of the invention by making each of the probes 50, 51 of equal length. As shown in FIG. 3, both of the bulkhead fittings 85 and 86 are so designed so that they will accept the probes and seat them in a fitting in such a way so as to assure that the orifice ends of the process are at the same depth below the surface of the fluid.

The fitting 85 includes a flange 120, the upper surface of which abuts the lower surface of the support block 80, and a threaded shaft 121 which extends through an opening in the block. A nut 122 secures the fitting in place. The opening in the lower end of the tube is enlarged to receive the probe 50, and a shoulder 125 is formed within to engage the end of the probe to ensure proper positioning of the orifice end of the probe the distance "d" below the support block 80.

A swageblock tube fitting 121 is used to provide for quick removal and replacement of the probes, thus allowing orifice sizes to be varied, if necessary, thereby permitting the largest practical ratio of orifice sizes to be used with any particular liquid. A similar swagelock tube fitting 127 is provided at the upper end of the bulkhead fitting to secure the hose 130 carrying process gas to the probe.

The underneath side of the support block 80 may be provided with a foam gasket 135 to form a pressure tight seal with the upper lip of the flow-through vessel 60, thus permitting that vessel to be pressurized.

The orifices are ground at the tips 140 or fabricated with a sharp edge to produce uniform radius bubbles irrespective of the wetting action of the process fluid. FIG. 4 illustrates the preferred construction. The probes may be fabricated from plastic, glass, metal, or other material compatible with the specific process fluid being tested. Preferably, the probe is of flint glass. The probes must be rigid, compatible with the fluid being used, and constructed so as to accommodate the necessary orifice diameters which are optimum for the liquid being tested.

In operation, once the probe assembly is in place, the process gas 10 is supplied under pressure to the pressure regulating means 15, and then through flow regulating means 30 and the flow dividing means 38 to the two probes 50, 51 which have orifices of different diameters located the same depth below the surface of the liquid under test in the containment vessel 60. The total flow rate is adjusted by micrometering valve 33; and the bubble rate at each orifice is adjusted by means of valves 40, 41 so that they are approximately equal. The flow regulating means will maintain the bubble rate of the gas to the tubes independently of the pressure within the vessel 60.

Figure 5:
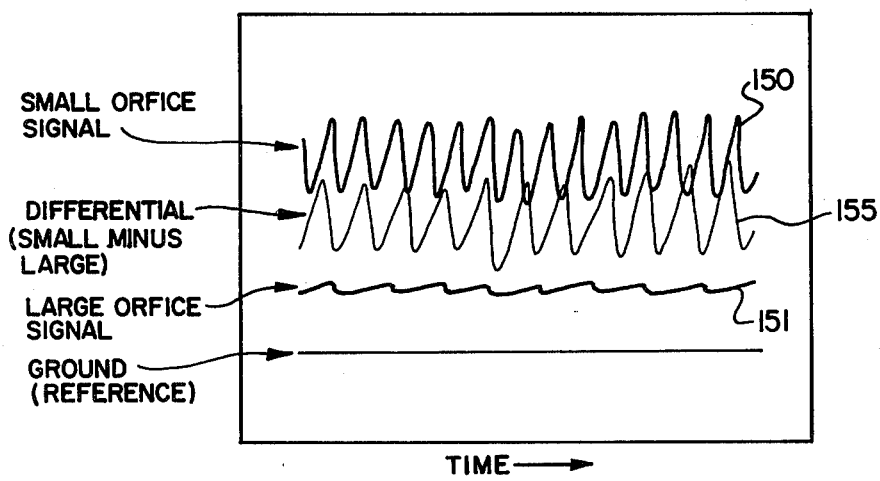
FIG. 5 is a combined waveform diagram of the pressure signals resulting from bubbling process gas through a liquid.

The pressure signal in each of the hoses 130, 131, which are connected to the probes 50, 51, respectively, is shown in FIG. 5.

Waveform 150 illustrates a typical pressure signal in hose 130 resulting from bubbles being formed at the signal orifice probe 50, and waveform 151 illustrates the pressure in hose 131 connected to the large orifice probe 51.

The maximum pressure occurs just prior to the bubble breaking away from the orifice and is a function of surface tension, and the minimum pressure is established by the size of the orifice. The time between maximum amplitudes is the bubble rate. Waveform 155 represents the difference between the waveforms 150 and 151, and therefore the output of differential pressure transducer 70.

Figure 6:
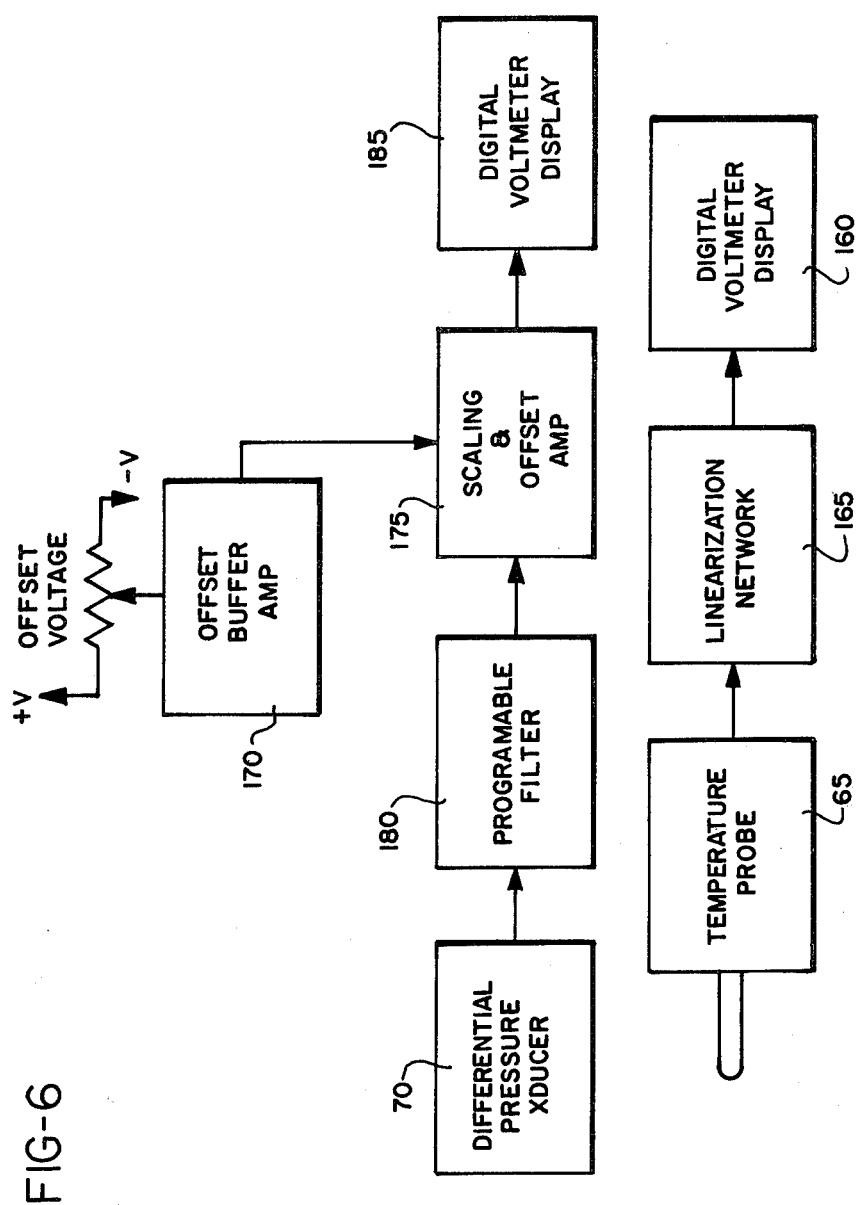
FIG. 6 is an electrical block diagram illustrating an electronic circuit for providing a direct display of liquid surface tension and temperature.

FIG. 6 is an electrical block diagram of one embodiment of a device to provide direct readout of liquid temperature and surface tension. In addition to a visual readout, this circuit can also supply appropriate analog and digital outputs for use by data printers, data storage devices, and process control circuitry.

The temperature probe 65 is preferably a resistance temperature device (RTD) having its output connected to digital display device 160 through an appropriate linearizing circuit 165. The response time of the temperature probe should be compatible with the response time of the surface tension measuring circuit in order to provide coordinated surface tension and temperature values.

The electrical output of the differential pressure transducer 70 is connected through a buffer amplifier 170, an offset and scaling amplifier 175, and programmable filter 180 to the digital display device 185. The offset and scaling amplifier 175 is provided with span adjustment potentiometer R1 and offset adjustment potentiometer R2 for calibration purposes. The third term of the modified Schroedinger equation referred to above may be eliminated by proper adjustment of the offset potentiometer R2.

The filter 180 is a Bessel filter having a low cut-off range of 0.02 to 0.05 Hertz to provide both stability and suitable response time. The Bessel filter gives a fast response (faster than a standard Butterworth filter) as it reaches equilibrium (steady state) condition within a span of 20 to 40 seconds, allowing surface tension readings within industry acceptable control response criteria.

The circuit of FIG. 6 is capable of recalibration over narrower ranges of surface tension, such as 20 to 40 dynes/cm or narrower in order to increase accuracy by taking a smaller portion of the non-linear surface tension calibration curve. The signal can be manipulated in further embodiments by breaking the non-linear curve into straight line increments to effectively eliminate the non-linearity due to the error term.

Figure 8:
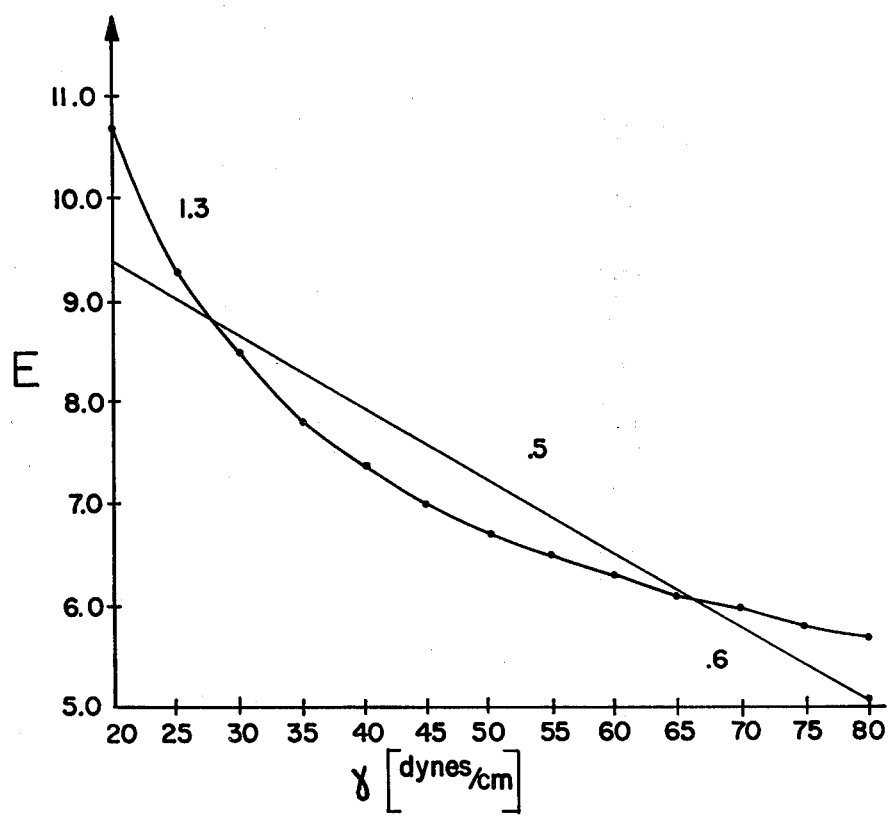
FIGS. 7, 8 and 9 are calibration curves for different combinations of probe orifice diameters.
Figure 7:
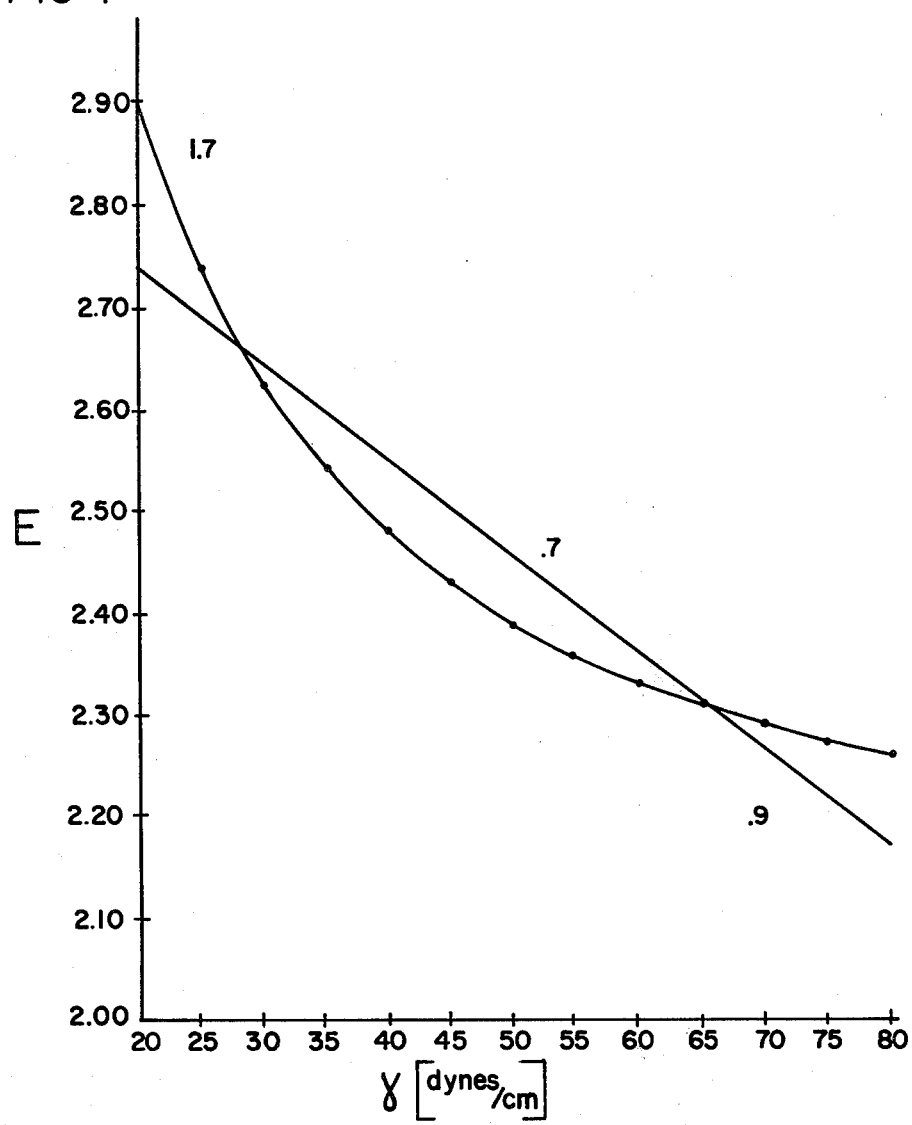
Figure 9:
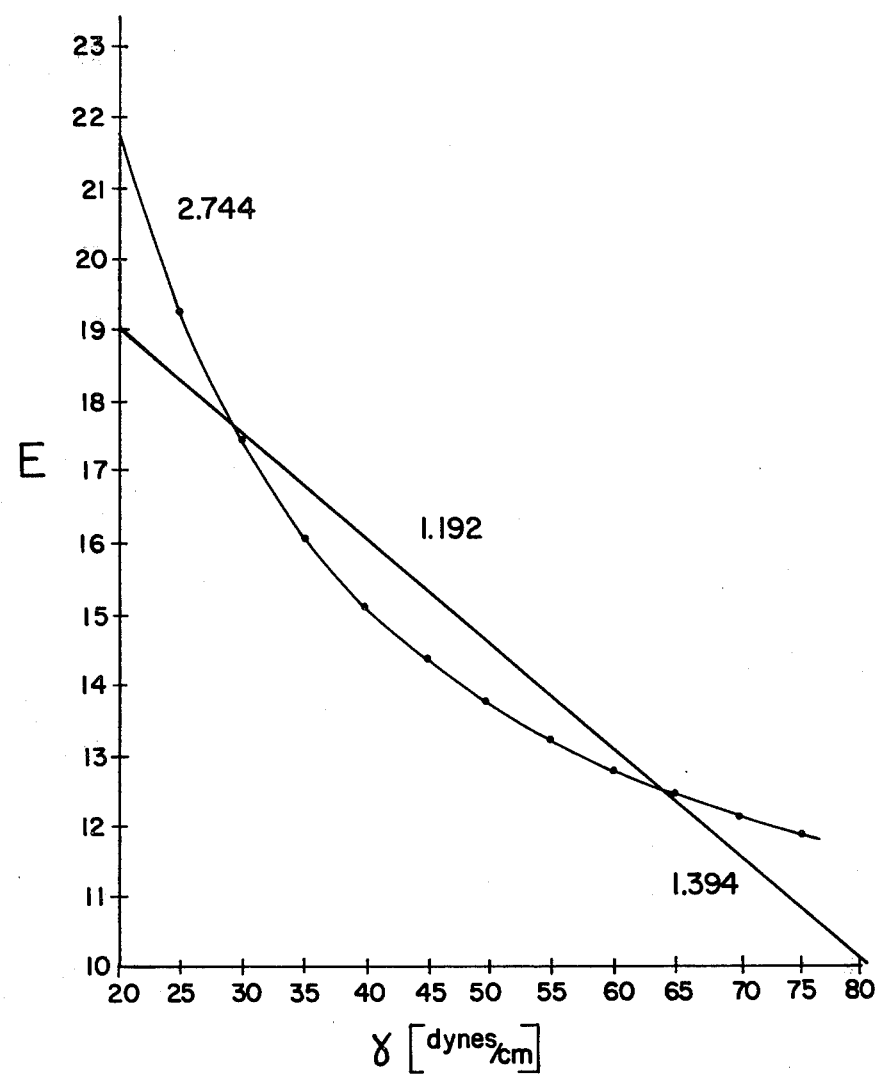

FIGS. 7, 8, and 9 are calibration curves for different combinations of orifice sizes. Each curve represents surface tension in the range of 20 to 80 dynes/cm along the horizontal axis, and the resulting error in dynes/cm along the vertical axis. Within each of these drawings, the curved line is the error term calibration curve, and the straight line represents the least squares fit through the calibration curve. In FIG. 7, the radius of the small orifice was 0.025 cm, and the large orifice was 0.25 cm. In FIG. 8, the radius of the small orifice was 0.025 cm, and the large orifice was 0.50 cm. In FIG. 9, the radius of the small orifice was 0.05 cm, and the large orifice was 0.50 cm. The largest ratio provide the smallest error between the least squares fit straight line and the error term calibration curve, as illustrated by FIG. 8.

The curves shown in FIGS. 7, 8 and 9 are developed by modifying the Schroedinger equation further so that:

$$\Delta P = \left[ \frac{\gamma - \rho g(r_2 - r_1)}{3(1/r_1 - 1/r_2)} - \frac{\rho^2 g^2(r_2^3 - r_1^3)}{24\gamma(1/r_1 - 1/r_2)} \right] [2(1/r_1 - 1/r_2)]$$

Setting the first term in the equation above to equal $\gamma^1$, results in:

$$E = \gamma - \gamma^1 = \frac{\rho g(r_2 - r_1)}{3(1/r_1 - 1/r_2)} + \frac{\rho^2 g^2(r_2^3 - r_1^3)}{24\gamma(1/r_1 - 1/r_2)}$$

Where $r_2 > r_1$ thereby allowing the error term to be plotted against the actual surface tension value, and correcting for error through electronic linearization techniques, a computer "look-up" table or other well-known commonly used methods.

Figure 10:
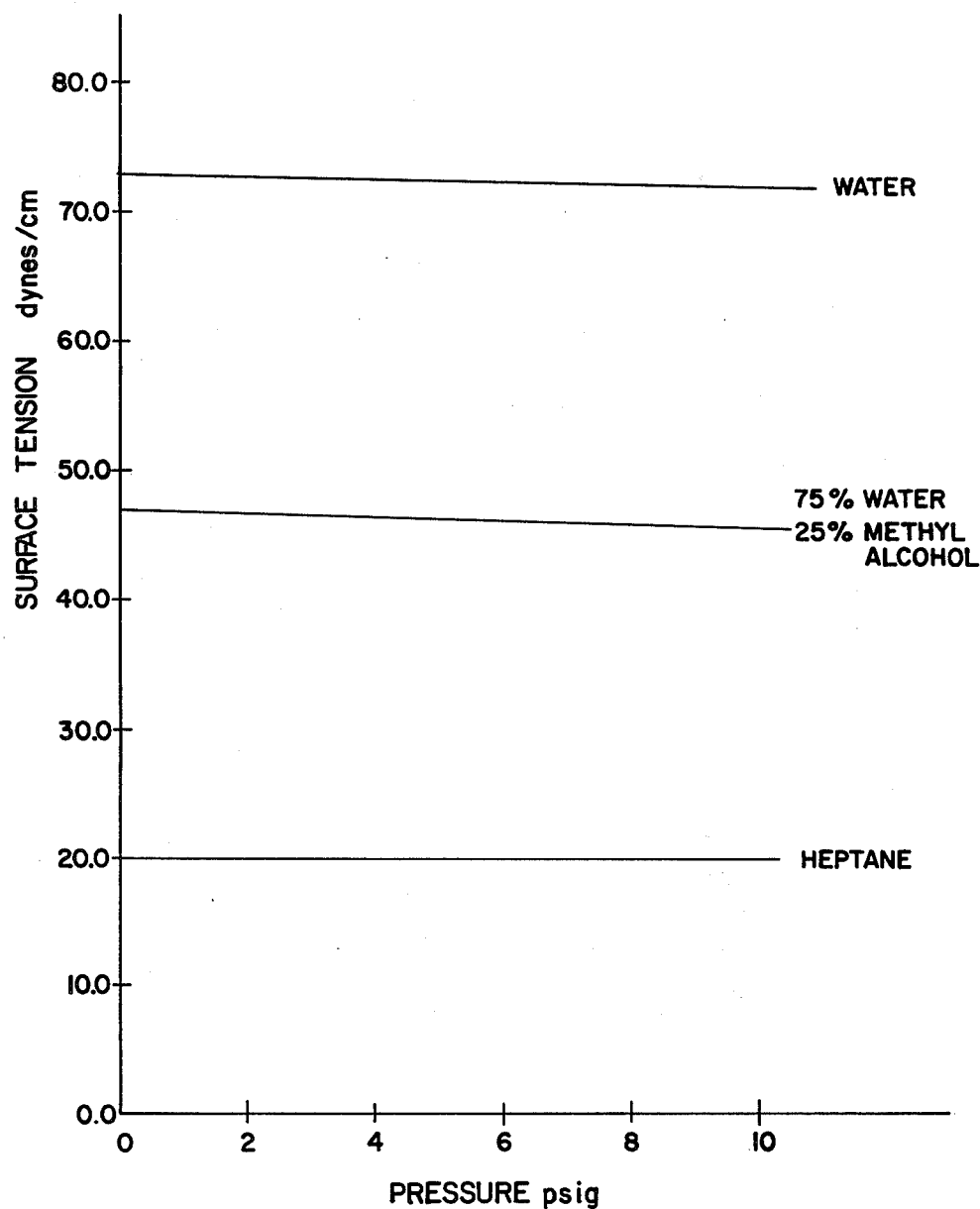
FIG. 10 is a graph showing the relationship of surface tension measurements with respect to pressure for three different liquids.

FIG. 10 demonstrates that this invention is capable of measuring surface tension at elevated and under varying pressures. Three fluids with different surface tensions, water (surface tension 72.1 dynes per centimeter at 25.0° C.), heptane (surface tension 19.7 dynes per centimeter at 25.0° C.), and a 75% water-25% methyl alcohol (surface tension 45.4 dynes per centimeter at 25° C.), are shown with pressure (psig) as the abscissa and surface tension (dynes per centimeter) as the ordinate. The fluids are pressurized from 0 to 10 psig in the pressure vessel using nitrogen (N) as the pressurizing atmosphere. According to the work of C. S. herrick and G. L. Gaines Jr., *Journal of Physical Chemistry*, 77,2703 (1974), the surface tension of water should decrease 0.068 dynes per centimeter for every pressure increase of 14.7 psi at 25° C. when the fluid is pressurized with a nitrogen atmosphere. This previous work was performed using a capillary rise surface tensiometer with a much longer response time than the device embodied here. The dependence of the surface tension with pressure for heptane and the alcohol-water mixtures has not been described previously in the literature. FIG. 10 demonstrates that the surface tensiometer as described can monitor surface tension as the pressure is increased from 0 to 10 psig without any adjustment to the instruments. The accuracy for this range of pressure is +2.0% of full scale reading. It should be noted that the invention is not limited to this range of pressure, but may have an extended operating pressure range.

If the orifices are not set to exactly equal depth, the error equation will have an added term as shown below:

$$E = \gamma - \gamma^1 = \frac{\rho g(h_1 - h_2)}{2(1/r_1 - 1/r_2)} + \frac{\rho g(r_2 - r_1)}{3(1/r_1 - 1/r_2)} + \frac{\rho^2 g^2(r_2^3 - r_1^3)}{24\gamma(1/r_1 - 1/r_2)\gamma}$$

Where $r_2 > r_1$

The term added on first term on the right side of the above equation will add a constant to the error value which will be a function of the difference in the orifice depths. The orifice depths are fixed each time the instrument is calibrated and will be in a fixed position until changed. Since this term is constant, the orifice depth error term will be compensated for during the calibration of the instrument.

While the form of apparatus herein described constitutes a preferred embodiment of this invention, it is to be understood that the invention is not limited thereto, and that changes may be made therein without departing from the scope of the invention.

What is claimed is:

1. An apparatus for determining the surface tension of a liquid comprising
    a pressure vessel for containing the liquid,
    a tube having an orifice positioned below the surface of the liquid,
    means for providing a source of gas under pressure to said tube,
    means connected between said source of gas and said tube for controlling the bubble rate of the gas to the tube independently of the pressure within said vessel,
    means for determining the pressure of the liquid at said orifice,
    means for measuring the pressure in said tube as compared to the pressure at said orifice as a function of the surface tension of the liquid.

2. An apparatus for determining the surface tension of a liquid comprising
    a flow-through pressure vessel for containing the liquid;
    a pair of tubes having orifices of different diameters positioned below the surface of the liquid;
    means for providing a source of gas under pressure to said tubes;
    means connected between said source of gas and said tubes for providing a regulated, constant volume flow rate of gas to the tubes independently of the pressure within said vessel;
    means for dividing the constant flow rate of gas between the two tubes;
    means for metering the flow of gas through each of the tubes whereby the bubble rate at each orifice can be adjusted to be approximately equal; and
    means for measuring the differential pressure in said tubes as a function of the surface tension of the liquid.

3. An apparatus for determining the surface tension of a liquid contained in a vessel wherein the pressure within the vessel may vary, said apparatus comprising
    a pair of tubes having orifices of different diameters positioned below the surface of the liquid;
    means for providing a source of gas under pressure to said tubes;
    means connected to said source of gas for providing a regulated, constant volume flow rate of gas to said tubes independently of the pressure within the vessel;
    means for dividing the constant flow rate of gas between the two tubes;
    means for metering the flow of gas through each of the tubes whereby the bubble rate at each orifice can be adjusted to be approximately equal; and
    means for measuring the differential pressure in said tubes as a function of the surface tension of the liquid.

4. In an apparatus for determining the surface tension of a liquid contained in a vessel wherein the pressure within the vessel may vary, said apparatus comprising:
    a pair of tubes having orifices of different diameters positioned below the surface of the liquid,
    means for providing a source of gas under pressure to said tubes, and means for measuring the differential pressure in said tubes as a function of the surface tension of the liquid, the improvement comprising:

means connected to said source of gas providing a regulated, constant pressure supply of gas, means connected to said constant pressure supply for providing a regulated, constant flow rate of gas to said tubes independent of the pressure within the vessel, means for dividing the constant flow rate of gas between the two tubes, and means for metering the flow of gas through each of the tubes whereby the bubble rate at each orifice can be adjusted to be approximately equal.

5. The apparatus of claim 4 wherein the orifices of both tubes are positioned the same distance below the surface of the liquid.

* * * * *

UNITED STATES PATENT AND TRADEMARK OFFICE
CERTIFICATE OF CORRECTION

PATENT NO. : 4,416,148
DATED : November 22, 1983
INVENTOR(S) : John P. Klus et al.

It is certified that error appears in the above-identified patent and that said Letters Patent are hereby corrected as shown below:

Col. 7, line 12, "process" should read -- probes --;

Col. 8, line 42, "recalibration" should read -- recalibrating --; and

Col. 9, line 44, "+2.0%" should read -- $\pm 2.0\%$ --.

Signed and Sealed this

Twenty-fourth Day of April 1984

[SEAL]

Attest:

GERALD J. MOSSINGHOFF

*Attesting Officer*  *Commissioner of Patents and Trademarks*